US005689902A

United States Patent [19]

Juang

[11] Patent Number: 5,689,902

[45] Date of Patent: Nov. 25, 1997

[54] FOOTWEAR FOR DOING EXERCISE AND FOOT-MASSAGING

[76] Inventor: Wen-Der Juang, 2F, No. 26-27, Lane 624, Sec2, Chung Shan Road, Jang Huah City, Taiwan

[21] Appl. No.: 713,291

[22] Filed: Sep. 13, 1996

[51] Int. Cl.[6] .......................... A43B 21/32; A43B 13/18; A61F 5/14

[52] U.S. Cl. .................................... 36/37; 36/28; 36/141

[58] Field of Search ................................ 36/27, 28, 141, 36/11.5, 35 R, 36 R, 37, 71, 34 R

[56] References Cited

U.S. PATENT DOCUMENTS

| | | | |
|---|---|---|---|
| 4,760,655 | 8/1988 | Mauch | 36/141 X |
| 4,815,221 | 3/1989 | Diaz | 36/37 X |
| 5,369,896 | 12/1994 | Frachey et al. | 36/28 X |
| 5,493,791 | 2/1996 | Kramer | 36/28 |

FOREIGN PATENT DOCUMENTS

| | | | |
|---|---|---|---|
| 510943 | 10/1992 | European Pat. Off. | 36/35 R |
| 2263619 | 8/1993 | United Kingdom | 36/37 |

*Primary Examiner*—B. Dayoan
*Attorney, Agent, or Firm*—W. Wayne Liauh

[57] ABSTRACT

A footwear has an outsole provided in the heel portion thereof with a recess for securing thereto a cushion block. The cushion block has a planar surface and an arcuate surface which is opposite in location to the planar surface and is provided with a plurality of rigid knobs made integrally therewith. The arcuate surface is defined by two straight peak edges opposite in location to each other. The cushion block is removably received in the recess of the outsole to allow the footwear to be used as an ordinary shoe, an exercise shoe, or a foot-massaging shoe.

6 Claims, 5 Drawing Sheets

FOOTWEAR FOR DOING EXERCISE AND FOOT-MASSAGING

FIELD OF THE INVENTION

The present invention relates generally to a footwear, and more particularly to the shoes for doing exercise and foot-massaging.

BACKGROUND OF THE INVENTION

The conventional shoes are mainly intended to protect the feet of a wearer of the shoes and can not be therefore used for massaging or exercising. For example, the running shoes have an outsole provided with a plurality of spikes or studs for doing the running exercise. In other words, the conventional shoes are not equipped to facilitate the wearer of the shoes to engage in the specific kinds of activities, such as exercising, foot-massaging, and so forth.

SUMMARY OF THE INVENTION

It is therefore the primary objective of the present invention to provide a footwear which can be used interchangeably for exercising and foot-massaging.

In keeping with the principle of the present invention, the foregoing objective of the present invention is attained by a footwear having a sole and a heel which is provided with a recess for mounting therein a cushion block. The cushion block has a planar surface and an arcuate surface which is opposite to the planar surface and is provided with a plurality of knobs made integrally therewith. The cushion block is removably received in the recess of the heel to allow the footwear to be used as an ordinary shoe, an exercise shoe, or a foot-massaging shoe.

The foregoing objective, features and functions of the present invention will be more readily understood upon a thoughtful deliberation of the following detailed description of the embodiment of the present invention in conjunction with the accompanying drawings.

DETAILED DESCRIPTION OF THE EMBODIMENT

Figure 2:
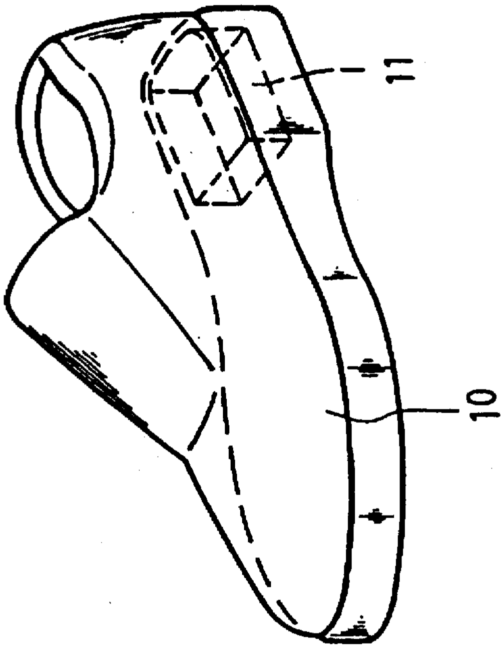
FIG. 2 shows a schematic view of a footwear of the present invention.
Figure 1:
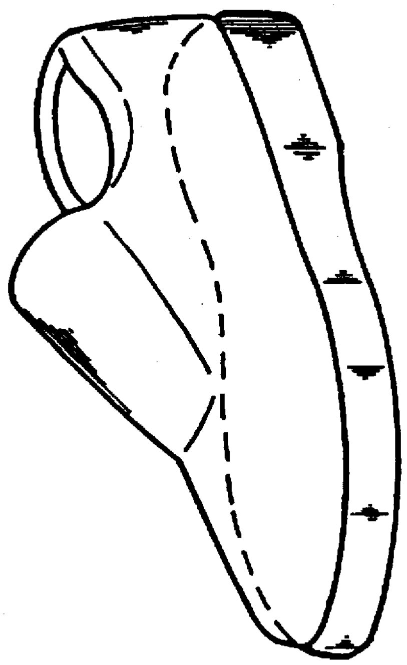
(Prior Art) Fig. 1
FIG. 1 shows a schematic view of a prior art footwear.
Figure 3:
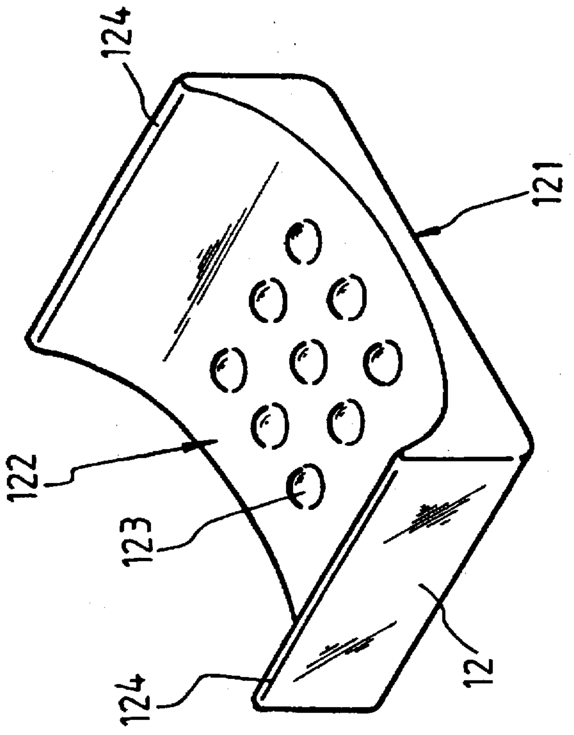
FIG. 3 shows a schematic view of the cushion block of the footwear of the present invention.

As shown in FIGS. 2–3, the footwear of the present invention has an outsole 10 which is provided in the heel portion thereof with a recess 11. The recess 11 is dimensioned to receive therein securely a cushion block 12. The cushion block 12 is removably mounted in the recess 11 and is composed of a planar surface 121 and an arcuate surface 122 opposite to the planar surface 121. The arcuate surface 122 is provided thereon with a plurality of rigid knobs 123 made integrally therewith. The arcuate surface 122 is defined by two straight peak edges 124 opposite in location to each other.

Figure 4:
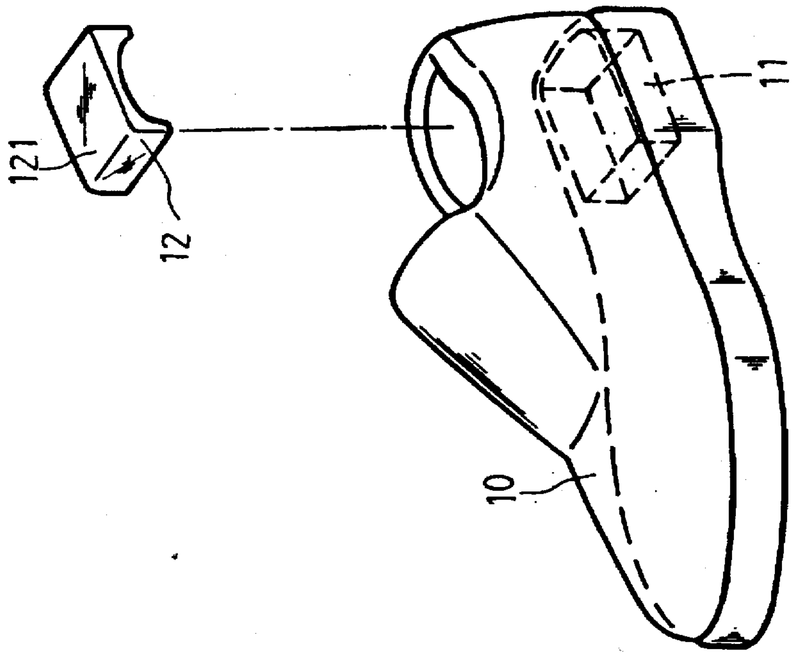
FIG. 4 shows a partial exploded view of the footwear of the present invention.
Figure 5:
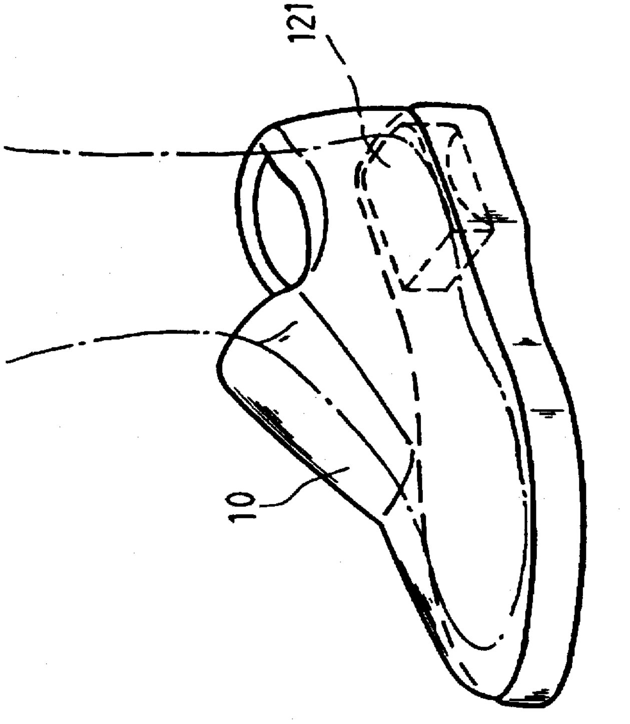
FIG. 5 shows a schematic view of the present invention in combination and in use.

Now referring to FIGS. 4 and 5, the cushion block 12 is secured to the recess 11 of the outsole 10 of the present invention such that the arcuate surface 122 of the cushion block 12 faces the ground surface. As a result, the footwear of the present invention is used as an ordinary footwear.

Figure 6:
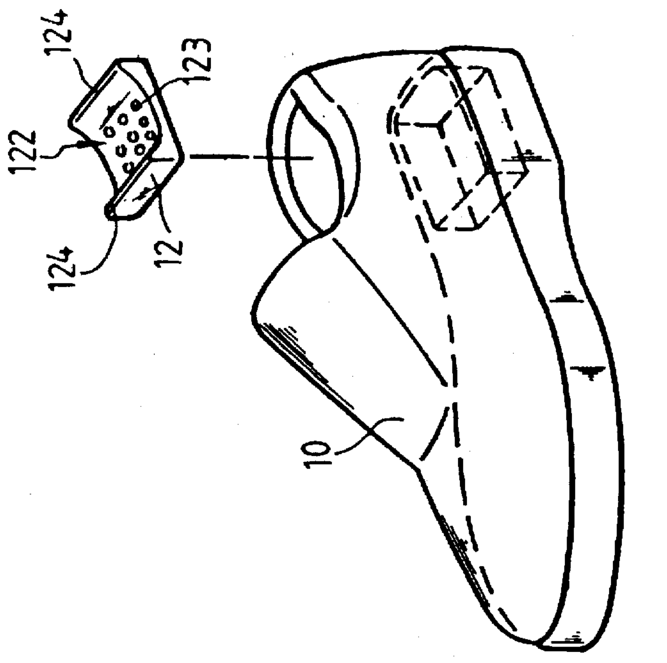
FIG. 6 shows another partial exploded view of the present invention.
Figure 8:
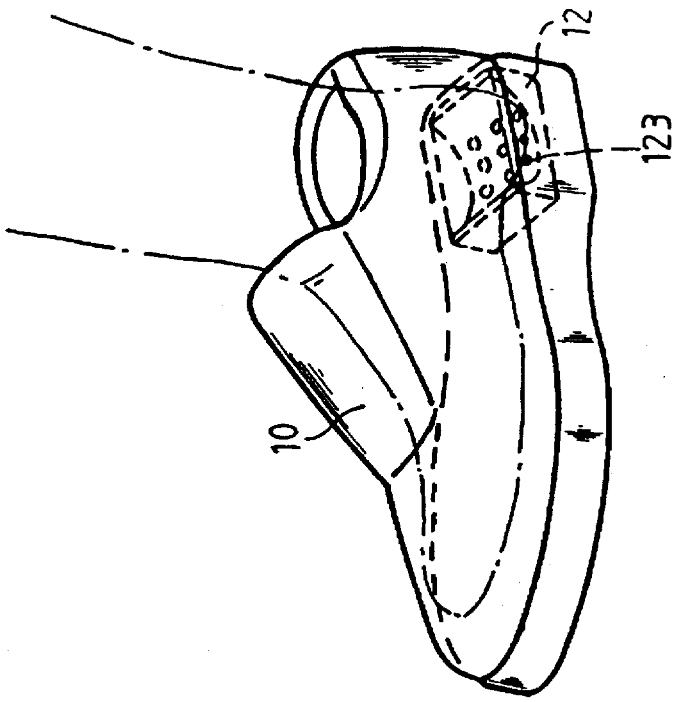
FIGS. 7–9 are schematic views illustrating the present invention at work.
Figure 7:
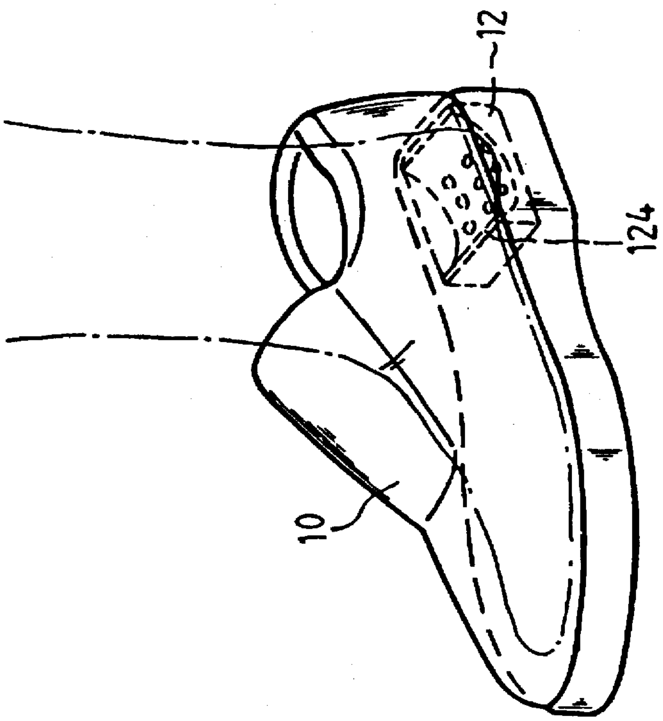

The cushion block 12 of the present invention is removably secured to the recess 11 of the outsole 10. For this reason, the cushion block 12 can be also secured to the recess 11 such that the planar surface 121 of the cushion block 12 faces the ground surface, as shown in FIG. 6. As a result, the footwear of the present invention can be used as a foot-massaging footwear. When the foot sole of a person wearing the footwear of the present invention exerts the pressure evenly on the outsole 10 of the present invention, the center of the foot sole of the person is stimulated by the peak edge 124 of the cushion block 12, as illustrated in FIG. 7. On the other hand, if the pressure of the foot sole of the person is centered on the heel portion of the outsole 10 of the footwear of the present invention, the foot heel of the person is stimulated by the rigid knobs 123 of the cushion block 12, as shown in FIG. 8.

Figure 9:
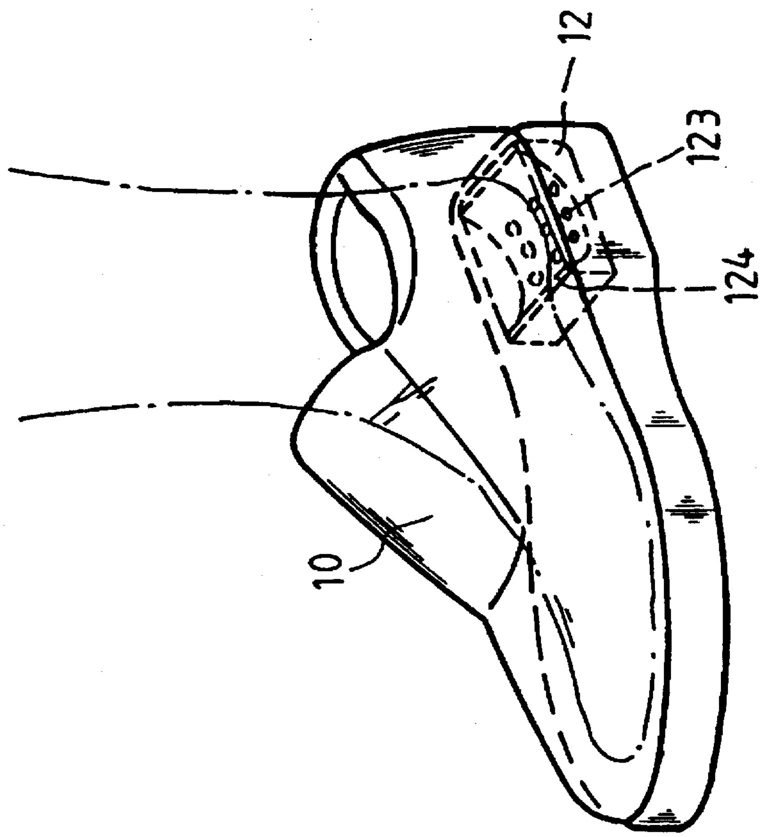

As illustrated in FIG. 9, the footwear of the present invention can be worn for doing an exercise, in view of the fact that the pressures of the front part of the foot sole and the foot toes are always centered on the front portion of the outsole 10 of the footwear of the present invention, and that the foot heel is bound to remain in the state of being suspended by the arcuate surface 122 of the cushion block 12.

The embodiment of the present invention described above is to be regarded in all respects as being merely illustrative and not restrictive. Accordingly, the present invention may be embodied in other specific forms without deviating from the spirit thereof. The present invention is therefore to be limited only by the scopes of the following appended claims.

What is claimed is:

1. A footwear having an outsole provided in a heel portion thereof with a recess dimensioned to receive therein securely and removably a cushion block, said cushion block having a planar surface and an arcuate surface opposite in location to said planar surface, said arcuate surface being provided thereon with a plurality of rigid knobs made integrally therewith, said arcuate surface being defined by two straight peak edges opposite in location to each other.

2. The footwear as defined in claim 1, wherein said cushion block is secured to said recess of said outsole such that said arcuate surface of said cushion block faces a ground surface when said outsole makes contact with said ground surface.

3. The footwear as defined in claim 1, wherein said cushion block is secured to said recess of said outsole such that said planar surface of said cushion block faces a ground surface when said outsole makes contact with said ground surface.

4. The footwear as defined in claim 3, wherein one of said two straight peak edges of said cushion block acts to massage the center of the foot sole of a person when said outsole is exerted on evenly by a pressure of the foot sole of the person.

5. The footwear as defined in claim 3, wherein said rigid knobs of said cushion block act to massage the foot heel of a person when the pressure of the foot sole of the person is centered on said heel portion of said outsole.

6. The footwear as defined in claim 3, wherein said arcuate surface of said cushion block acts to suspend the foot heel of a person when the pressure of the front part of the foot sole of the person is centered on a front portion of said outsole.

* * * * *